United States Patent [19]

Frischling et al.

[11] Patent Number: 4,659,573

[45] Date of Patent: Apr. 21, 1987

[54] MINERAL OIL SUBSTITUTE FOR TOILETRIES AND COSMETICS

[75] Inventors: Louis B. Frischling, Lawrence; Stephen M. Greenberg, New York, both of N.Y.

[73] Assignee: Lipo Chemicals, Inc., Paterson, N.J.

[21] Appl. No.: 701,389

[22] Filed: Feb. 14, 1985

[51] Int. Cl.[4] .................... A61K 7/021; A61K 7/031; A61K 7/06; A61K 7/15

[52] U.S. Cl. .......................................... 424/63; 424/64; 424/70; 424/73; 514/844; 514/846; 514/847; 514/887; 514/939; 514/943; 560/76; 560/198

[58] Field of Search ............... 514/844, 846, 847, 887, 514/943, 939; 560/76, 198; 424/70, 73, 64, 63

[56] References Cited

U.S. PATENT DOCUMENTS

| | | | |
|---|---|---|---|
| 3,682,694 | 8/1972 | Kato et al. | 560/76 |
| 3,957,854 | 5/1976 | Miller | 560/198 |
| 3,981,838 | 9/1976 | Wilson | 560/76 |
| 4,275,189 | 6/1981 | Danick et al. | 560/76 |
| 4,338,431 | 7/1982 | König | 560/76 |
| 4,370,319 | 1/1983 | Chapin et al. | 514/943 |

*Primary Examiner*—Dale R. Ore
*Attorney, Agent, or Firm*—Anthony Lagani, Jr.

[57] ABSTRACT

This invention relates to a substitute for mineral oil in toiletry and cosmetics. In particular it relates to blends of esters which match the viscosity and feel of mineral oil. Specifically, it relates to ester blends which include tridecyl trimellitate.

Tridecyl trimellitate ("TDTM") is the ester of tridecyl alcohol and trimellitic acid, and has recently been offered for use to the cosmetics industry.

It has surprisingly been found that by blending tridecyl trimellitate with other esters, the viscosity and feel of mineral oil can be matched, the resulting product being a substitute for mineral oil in toiletry and cosmetic compositions.

19 Claims, No Drawings

MINERAL OIL SUBSTITUTE FOR TOILETRIES AND COSMETICS

FIELD OF THE INVENTION

This invention relates to a substitute for mineral oil in toiletry and cosmetic compositions.

BACKGROUND OF THE INVENTION

Mineral oil is one of the most basic and commonly used ingredients in cosmetics. It is used for a variety of purposes including imparting specific textural and aesthetic qualities to cosmetic products. Illustrative of these qualities imparted to cosmetics by mineral oil are slip, emolliency, viscosity changes, residual feel and variations in rate of adsorption. Additionally, mineral oil is a solvent for many of the raw materials used in cosmetics. Mineral oil finds application in all forms of cosmetic products such as creams, lotions, cleansing creams, night creams or lotions, moisturizing creams or lotions, shaving products, make-up products, e.g., lipstick, rouges, etc.

The type of emollient products in which mineral oil is used are described as having various "feels" such as slip, drag, tack, lack of tack, etc. While the feel of a particular emollient will depend an the overall formulation, the mineral oil is an important contributing component to give the emollient the desired properties. Although there has been a recent resurgence of the use of natural oils in cosmetics, this has been primarily limited to the health oriented market. Since the turn of the century, mineral oil has dominated the market for oils used in toiletries and cosmetics because it is odorless, water white, chemically inert and relatively inexpensive.

There has been some recent concern over the health aspects of the use of mineral oil on the skin. Health oriented magazines such as *Prevention* (Rodale Press) have featured articles concerning the hazards in its use. Whether the hazards involved in the use of mineral oil in toiletries and cosmetics is a legitimate concern is open to question. However, the perceived hazard has generated a demand for a mineral oil substitute for these uses, especially in those products which are advertised as containing natural ingredients.

Heretofore the need has gone unfulfilled. Substitutes offered to the trade have lacked some important characteristic generally attributed to mineral oil such as emolliency, slip, cushion, rate of adsorption, penetration, etc. Since the viscosity of the mineral oil has an effect on the overall characteristics of the product in which it is used, it is preferred to match oil viscosity in any substitute product. The mineral oils currently used in toiletry and cosmetic products have a viscosity range of about 70 S.S.U. to about 350 S.S.U. at 100° F.

The lack of success in developing a substitute for mineral oil has been in part because compounds, other than mineral oil, approved for use in the cosmetics trade are either of too low viscosity to allow them to match mineral oil properties, or where they have high viscosities they have a tacky or gummy feel.

SUMMARY OF THE INVENTION

It has surprisingly been found that by blending tridecyl trimellitate with other esters, the viscosity and feel of mineral oil can be matched, the resulting product being a substitute for mineral oil in toiletry and cosmetic compositions. Particularly advantageous results are achieved when the tridecyl trimellitate is blended with dipentaerythritol hexacaprylate/hexacaprate, tridecyl stearate and neopentylglycol dicaprylate/dicaprate.

DETAILED DESCRIPTION OF THE INVENTION

This invention relates to a substitute for mineral oil in toiletry and cosmetics. In particular it relates to blends of esters which match the viscosity and feel of mineral oil. Specifically, it relates to ester blends which include tridecyl trimellitate.

Tridecyl trimellitate ("TDTM") is the ester of tridecyl alcohol and trimellitic acid, and has recently been offered for use to the cosmetics industry. It is a very heavy viscosity, syrupy, odorless liquid which is slightly tacky in application, but leaves the skin feeling very soft. Tridecyl stearate ("TDS") is the stearic acid ester of tridecyl alcohol, and is a commonly used ingredient in the cosmetic trade. It has a velvety afterfeel and is recommended for use in all products which are left on throughout the day such as moisturizers, lotions, make-ups, face creams and day creams.

Dipentaerythritol hexacaprylate/hexacaprate ("DPHC") and neopentylglycol dicaprylate/dicaprate ("NPGC") are two esters recently made available to the toiletry and cosmetic trade and are useful in the practice of this invention for blending with TDTM. DPHC is a medium to heavy viscosity, odorless liquid which leaves the skin feeling emollient soft and slightly oily. NPGC has excellent absorption properties and leaves a very elegant, silky afterfeel to the skin.

In the practice of this invention, TDTM is blended with at least one other ester, preferably at least two other esters, to formulate a blend which duplicates the viscosity and feel of mineral oil for use in toiletry and cosmetics. The esters generally blended with TDM will be lower in viscosity than TDTM. While a wide range of esters may be blended with TDTM, the preferred esters are TDS, NPGC and DPHC. The selection and quantity of the esters which are blended with TDTM will vary depending on desired viscosity of the final product and the feel which the product is intended to have.

Illustrative, non-limiting examples of other esters which may be blended with TDTM are isodecyl trimellitate, isopropyl myristate, isopropyl palmitate, tridecyl myristate, tridecyl palmitate, isodecyl trimellitate, propylene glycol dicaprate/dicaprylate, neopentyl glycol dicaprate and trisodecyl trimellitate.

Depending on the desired viscosity and other properties desired, the amount of TDTM in a particular formulation can vary from about 5 to about 85 wt%, based on the ester blend, preferably about 5 to about 60 wt%, more preferably about 8 to about 45 wt%, most preferably about 10 to about 38 wt%, e.g., about 12 to about 37 wt%. Where the ester blend is a low viscosity blend, e.g., 70 S.S.U. at 100° F., the TDTM is preferably utilized at about 10 to about 14 wt%. For an intermediate viscosity blend, e.g., 130 S.S.U. at 100° F., the TDTM is preferably utilized at about 33 to about 38 wt% based on the ester blend, and for a high viscosity blend, e.g., 350 S.S.U. at 100° F., the TDTM is preferably utilized at about 38 to about 42 wt%, based on the ester blend. The balance of the ester blend can be at least one additional ester, preferably at least two additional esters, each of the two esters being utilized at about 2 to about 60 wt% based on the ester blend depending on the particular properties desired. In a preferred embodiment where TDS is one of the two or more additional esters blended with the TDTM, it can be utilized at about 5 to about 55 wt%. Where the ester blend is a low viscosity blend, e.g., less than 150 S.S.U., the TDS is preferably utilized at about 40 to about 50 wt%, more preferably about 42 to about 46 wt%, based on the ester blend. Where the ester blend is a higher viscosity blend, the TDS is preferably utilized at about 5 to about 20 wt%, more preferably at about 5 to about 12 wt%, most preferably at about 6 to about 9 wt% based on the ester blend.

Where NPGC is one of the additional esters, it is preferably utilized at about 2 to about 55 wt% based on the ester blend. For lower viscosity blends, the NPGC is preferably utilized at about 40 to about 50 wt% based on the ester blend, more preferably about 42 to about 45 wt%. For higher viscosity blends, the NPGC is preferably utilized at about 2 to about 10 wt%, more preferably about 3 to about 5 wt%.

Where DPHC is one of the additional ester blends it can be utilized at about 10 to about 55 wt%. For lower viscosity blends the DPHC is preferably utilized at about 12 to about 25 wt% based on the ester blend, more preferably at about 16 to about 20 wt%, most preferably at about 17 to about 19 wt% based on the ester blend. For higher viscosity blends, the DPHC is preferably utilized at about 40 to about 55 wt% based on the ester blend, more preferably about 42 to about 52 wt%, most preferably about 46 to about 50 wt%.

The ester blends of this invention are suitable for use in a wide range of toiletry and cosmetic products including night creams, moisturizers, lotions, make-ups, face creams, day creams, body lotions, lipsticks and lip glosses. The advantages of the instant invention may be more readily appreciated by reference to the following examples.

EXAMPLE I

A formulation was prepared using TDTM, TDS and NPGC which matched the viscocity and feel of a 70 S.S.U. mineral oil.

| Ester Component | Weight Percent |
|---|---|
| TDTM | 12.50 |
| TDS | 43.75 |
| NPGC | 43.75 |
|  | 100.00 |

The blend matched the tactile properties of 70 S.S.U. mineral oil. The viscosity of the blends was 78 S.S.U. at 100° F.

EXAMPLE II

An ester blend was prepared to match the viscosity and feel of 130 S.S.U. mineral oil.

| Ester Component | Weight Percent |
|---|---|
| TDTM | 36.4 |
| DPHC | 18.2 |
| TDS | 45.4 |
|  | 100.0 |

The blend matched the tactile properties of 130 S.S.U. oil and had a viscosity of 195 S.S.U. While the viscosity of the blend does not meet the target (130 S.S.U. at 100° F.), it is in a range which permits it to be a substitute for 130 viscosity oil by manipulation of the formulation in which it is used.

EXAMPLE III

A blend was prepared to match 350 S.S.U. mineral oil.

| Ester Component | Weight Percent |
|---|---|
| TDTM | 39.70 |
| DPHC | 48.00 |
| TDS | 8.45 |
| NPGC | 3.85 |
|  | 100.00 |

The blend matched the tactile properties of 350 S.S.U. oil and had a viscosity of 340 S.S.U.

The following formulations illustrate the use of the ester blends of this invention in various cosmetic and toiletry products. All components are described using their CTFA designations.

| Formulation I - Waterless Hand Cleaner | | |
|---|---|---|
| Component | wt % | Mixing Sequence |
| PEG-40 Stearate | 3.1 | 1 |
| Glyceryl Stearate | 6.0 | 1 |
| Hydrogenated Lanolin | 2.2 | 1 |
| PEG-24 Hydrogenated Lanolin | 3.1 | 1 |
| Oleic Acid | 6.0 | 1 |
| Propylparaben | 0.1 | 1 |
| Deoderized Kerosene | 11.0 | 1 |
| Ester Blend | 6.3[1] | 1 |
| Triethanolamine | 3.0 | 2 |
| Methylparaben | 0.1 | 2 |
| Deionized Water | 59.1 | 2 |
| Fragrance | q.s. | 3 |
| Color | q.s. | 4 |

[1] Ester blend of Example 1.

The components are used in the order of the mixing sequence number shown. The sequence 1 materials are blended under slow agitation while heating to about 75° C. in a covered blending tank to reduce evaporation loss. The sequence 2 components are blended in a separate vessel to about 77° C. under slow agitation. The sequence 2 components are then added to the sequence 1 components with rapid agitation, e.g., Lightning ® mixer for about 15 minutes maintaining the temperature at about 75° C. The emulsion formed is cooled to about 45° C. with mixing and the fragrance and color added separately. The composition is then cooled to 30° C. with continuous mixing. The product has utility as a hand cleaner to remove grease and dirt.

| Formulation II - Vitamin E Aloe Cream | | |
|---|---|---|
| Component | wt % | Sequence |
| Deionized Water | 81.70 | 1 |
| Glycerin | 4.00 | 1 |
| Aloe Vera Gel | 1.00 | 1 |
| Triethanolamine 88% | 0.50 | 1 |
| Methylparaben | 0.25 | 1 |
| Formalin | 0.20 | 1 |
| Propylparaben | 0.10 | 1 |
| Glyceryl Stearate | 4.00 | 2 |
| Ester Blend | 4.00[1] | 2 |
| Stearic Acid XXX | 2.00 | 2 |
| Coconut Oil | 1.00 | 2 |
| Tocopheryl Acetate | 0.25 | 2 |
| Cocoa Butter | 0.25 | 2 |
| PEG 75 Lanolin | 0.25 | 2 |
| Cetyl alcohol | 0.25 | 2 |

-continued

| Formulation II - Vitamin E Aloe Cream | | |
|---|---|---|
| Component | wt % | Sequence |
| Perfume | 0.25 | 3 |

(1)Ester blend of Example II.

The components are blended in accordance with their sequence numbers. Sequence 1 components are blended using a lightening mixture at a temperature of about 80° C. while sequence 2 components are treated in a separate vessel to about 78° C. The Sequence 2 component blend is then added slowly to the Sequence 1 components. Mixing is continued without heating for about 10 minutes. The blend is then cooled to about 45° C. and the perfume is added. Mixing is continued until the blend has cooled to about 25° C.

The ester blends of this invention can be used in a wide range of other cosmetics such as non-foaming shaving gels, curl activators, moisturizing creams, etc. Formulations for these and other cosmetic compositions which use mineral oil are well known in the art. Generally, the ester blends of this invention can be utilized as a direct substitution. In some cases a slight adjustment in the hydrophilic-lipophilic balance (HLB) of the emulsifier system will be required to maintain emulsion stability. Such minor modifications can be accomplished without undue experimentation by those skilled in the art.

A suggested mineral oil containing non-foaming shaving gel formulation is as follows:

| Component | wt % |
|---|---|
| Lauramide DEA | 5.50 |
| Sodium Laurethylphosphate | 4.50 |
| Oleyl Alcohol | 3.00 |
| Steareth-20 | 6.50 |
| Isopropyl Myristate | 5.00 |
| Glycereth-26 | 10.00 |
| Mineral Oil | 15.00 |
| Distilled Water | 47.00 |
| Color | q.s. |
| Preservative | q.s. |
| Fragrance | q.s. |

While the foregoing examples I to III set forth specific formulations to match the tactile properties of mineral oil at different viscosities, it will be appreciated that "feel" is subjective and slight variations in formulations will result in tactile properties which certain users will find preferable to those of mineral oil. It is therefore within the scope of this invention to prepare ester blends of TDTM which do not match the tactile properties of mineral oil but are nonetheless useful in cosmetic compositions for their own attributes.

As used in the specification and claims, the term "cosmetic products" means those consumer products used as cosmetics, skin care products, toiletry and beauty aids including but not limited to shave creams, moisturizers, curl activators, hand cleaners, lipsticks, rouges, night creams and their equivalents as lotions.

What is claimed is:

1. An ester blend suitable for use as a mineral oil substitute in cosmetics and toiletries comprising tridecyl trimellitate blended with at least one additional ester selected from the group consisting of dipentaerythritol hexacaprylate/hexacaprate, tridecyl stearate and neopentyl glycol dicaprylate/dicaprate, said blend comprising about 5 to about about 85 wt. % tridecyl trimellitate based on the weight of the blend.

2. The ester blend according to claim 1 wherein two additional esters are blended with the tridecyl trimellitate and each additional ester is incorporated into the blend at about 2 to about 60 wt%.

3. The ester blend according to claim 1 where three additional esters are blended with the tridecyl trimellitate.

4. The ester blend according to claim 2 wherein the two additional esters are tridecyl stearate (TDS) incorporated into the blend at about 5 to about 55 wt% and neopentylglycol dicaprylate/dicaprate (NPGC) incorporated into the blend at about 2 to about 55 wt%.

5. The ester blend according to claim 4 wherein the TDTM is utilized at about 10 to about 14 wt%, the TDS is utilized at about 40 to about 50 wt% and the NPGC is utilized at about 40 to about 50 wt%.

6. The ester blend according to claim 5 wherein the TDTM is utilized at about 11 to about 13 wt% based on the ester blend, the TDS is utilized at about 42 to about 46 wt% based on the ester blend, and the NPGC is utilized at about 42 to about 46 wt% based on the ester blend.

7. The ester blend according to claim 2 wherein the two additional esters are tridecyl stearate (TDS) and dipentaerythritol hexacaprylate/hexacaprate (DPHC).

8. The ester blend according to claim 7 wherein the TDTM is utilized at about 33 to about 38 wt% based on the ester blend, the TDS is utilized at about 40 to about 50 wt% based on the blend, and the DPHC is utilized at about 12 to about 25 wt%.

9. The ester blend according to claim 8 wherein the TDS is utilized at about 42 to about 46 wt% and the DPHC is utilized at about 16 to about 20 wt% based on the ester blend.

10. The ester blend according to claim 9 wherein the DPHC is utilized at about 17 to about 19 wt%.

11. The ester blend according to claim 3 wherein the three additional esters are TDS, DPHC and NPGC.

12. The ester blend according to claim 11 wherein the TDTM is utilized at about 38 to about 42 wt% based on the ester blend, the TDS is utilized at about 5 to about 20 wt%, the NPGC is utilized at about 2 to about 10 wt% and the DPHC is utilized at about 40 to about 55 wt% based on the blend.

13. The ester blend according to claim 12 wherein the TDS is utilized at about 5 to about 12 wt% based on the ester blend.

14. The ester blend according to claim 13 wherein the TDS is utilized at about 6 to about 9 wt% based on the ester blend.

15. The ester blend according to claim 12 wherein the NPGC is utilized at about 3–5 wt%.

16. The ester blend according to claim 12 wherein the DPHC is utilized at about 42–52 wt% based on the ester blend.

17. The ester blend according to claim 16 wherein the DPCH is utilized at about 46 to about 50 wt%.

18. The ester blend according to claim 12 wherein the TDS is utilized at about 6 to about 9 wt% based on the ester blend, the NPGC is utilized at about 3 to about 5 wt% based on the ester blend, and the DPHC is utilized at about 46 to about 50 wt% based on the ester blend.

19. In a toiletry or cosmetic product having as a constituent thereof mineral oil, the improvement which comprises substituting for the mineral oil, the ester blend according to claim 1, said ester blend having substantially the same viscosity as the mineral oil.

* * * * *